United States Patent
Song et al.

(10) Patent No.: US 12,203,901 B2
(45) Date of Patent: Jan. 21, 2025

(54) JIG FOR EVALUATING BUFFER PAD, AND METHOD OF EVALUATING BUFFER PAD USING THE SAME

(71) Applicant: LG ENERGY SOLUTION, LTD., Seoul (KR)

(72) Inventors: Seung Ho Song, Daejeon (KR); Myung Su Hong, Daejeon (KR)

(73) Assignee: LG ENERGY SOLUTION, LTD., Seoul (KR)

( * ) Notice: Subject to any disclaimer, the term of this patent is extended or adjusted under 35 U.S.C. 154(b) by 309 days.

(21) Appl. No.: 17/796,109

(22) PCT Filed: Aug. 24, 2021

(86) PCT No.: PCT/KR2021/011318
§ 371 (c)(1),
(2) Date: Jul. 28, 2022

(87) PCT Pub. No.: WO2022/059951
PCT Pub. Date: Mar. 24, 2022

(65) Prior Publication Data
US 2023/0081338 A1    Mar. 16, 2023

(30) Foreign Application Priority Data

Sep. 17, 2020 (KR) .................. 10-2020-0119694

(51) Int. Cl.
*G01N 3/12* (2006.01)
*G01N 3/04* (2006.01)
(Continued)

(52) U.S. Cl.
CPC ........... *G01N 3/12* (2013.01); *G01N 3/04* (2013.01); *H01M 50/242* (2021.01);
(Continued)

(58) Field of Classification Search
CPC .................. G01N 3/12; G01N 2203/0019
See application file for complete search history.

(56) References Cited

U.S. PATENT DOCUMENTS 9,666,470 B2 * 5/2017 Thallner ........... H01L 21/68721
9,868,881 B2   1/2018 Kim et al.
(Continued)

FOREIGN PATENT DOCUMENTS

JP   S53016939 Y   5/1979
JP   S58116648 U   8/1983
(Continued)

OTHER PUBLICATIONS

International Search Report (with partial translation) and Written Opinion dated Dec. 3, 2021 issued in corresponding International Patent Application No. PCT/KR2021/011318.
(Continued)

*Primary Examiner* — Kristina M Deherrera
*Assistant Examiner* — Jean F Morello
(74) *Attorney, Agent, or Firm* — MORGAN, LEWIS & BOCKIUS LLP

(57) ABSTRACT

The present invention relates to a jig for evaluating a buffer pad. The jig includes a first plate configured to be positioned on one surface of the buffer pad and configured to press the buffer pad; a second plate configured to be positioned on another surface of the buffer pad and configured to press the buffer pad from the other surface; and a magnet member configured to be positioned between the first plate and the second plate. A recessed portion, which is recessed to allow the magnet member to be disposed, is defined at an edge of at least one of the first plate and the second plate.

19 Claims, 9 Drawing Sheets

(51) Int. Cl.
  *H01M 50/242*   (2021.01)
  *H01M 50/258*   (2021.01)
(52) U.S. Cl.
  CPC .. *H01M 50/258* (2021.01); *G01N 2203/0019* (2013.01); *G01N 2203/0085* (2013.01); *G01N 2203/0282* (2013.01); *G01N 2203/04* (2013.01)

(56) References Cited

U.S. PATENT DOCUMENTS

| | | |
|---|---|---|
| 2011/0128021 A1 | 6/2011 | Chou |
| 2017/0123001 A1 | 5/2017 | Chigullapalli et al. |
| 2020/0176745 A1 | 6/2020 | Lee |

FOREIGN PATENT DOCUMENTS

| | | |
|---|---|---|
| JP | 2001-330541 A | 11/2001 |
| JP | 2006-011312 A | 1/2006 |
| JP | 2012-154892 A | 8/2012 |
| JP | 2014-060253 A | 4/2014 |
| JP | 2016-173289 A | 9/2016 |
| JP | 2017-514134 A | 6/2017 |
| KR | 10-2007-0013437 A | 1/2007 |
| KR | 10-2009-0054309 A | 5/2009 |
| KR | 10-2009-0062504 A | 6/2009 |
| KR | 10-2014-0019453 A | 2/2014 |
| KR | 10-2015-0049985 A | 5/2015 |
| KR | 10-2016-0001975 A | 1/2016 |
| KR | 10-2017-0016563 A | 2/2017 |
| KR | 10-1800651 B1 | 11/2017 |
| KR | 10-2019-0054709 A | 5/2019 |
| KR | 10-2020-0081647 A | 7/2020 |
| WO | 2015/163845 A1 | 10/2015 |

OTHER PUBLICATIONS

Office Action issued in corresponding Japanese Patent Application No. 2022-545427 dated Jul. 10, 2023. Note: JP 2014-060253 A cited therein is already of record.

* cited by examiner

[FIG. 1]
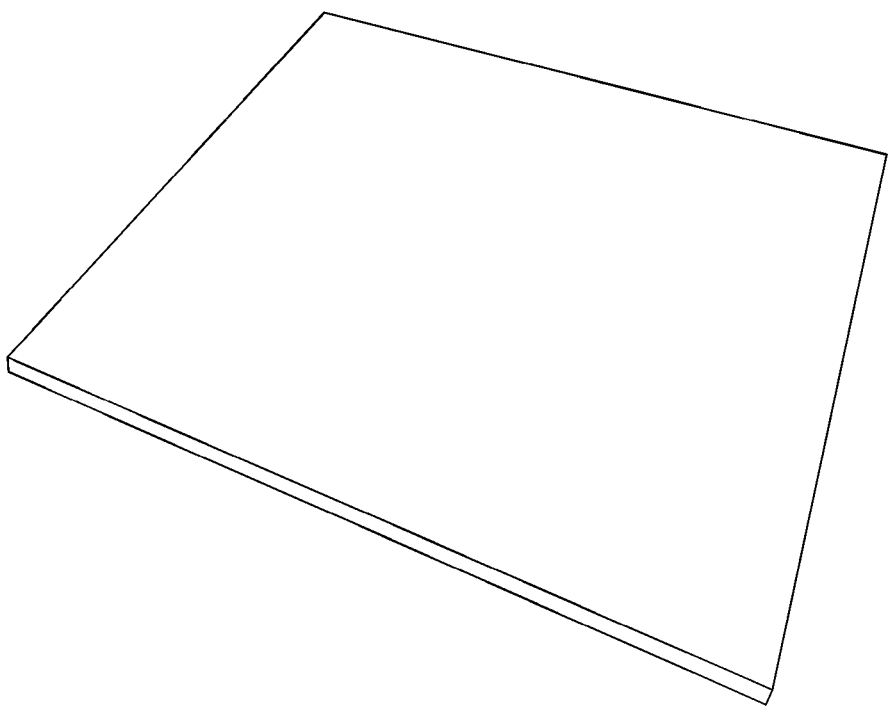

[FIG. 2]
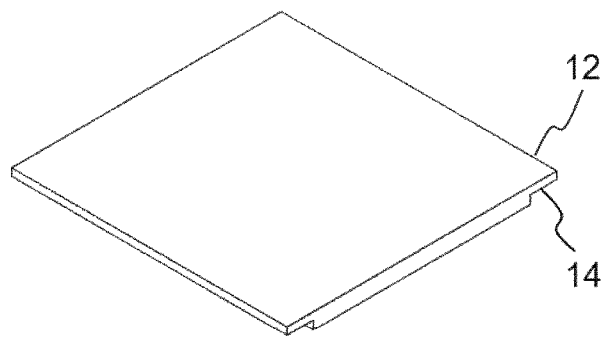
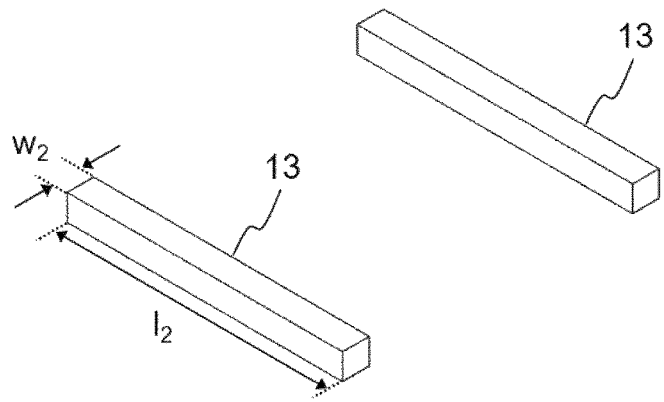
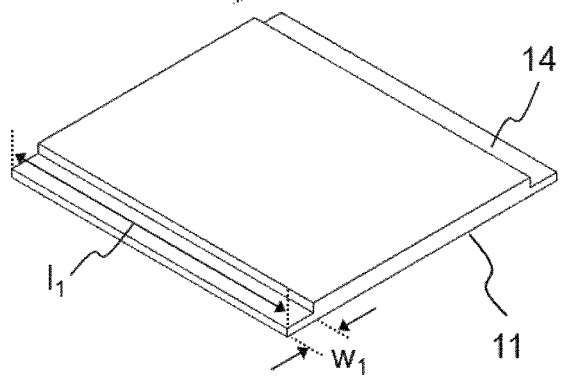

[FIG. 3]
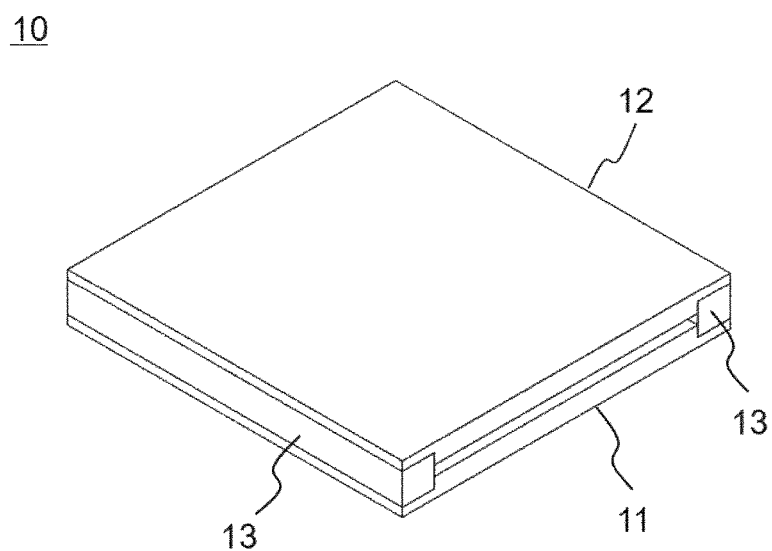

[FIG. 4]
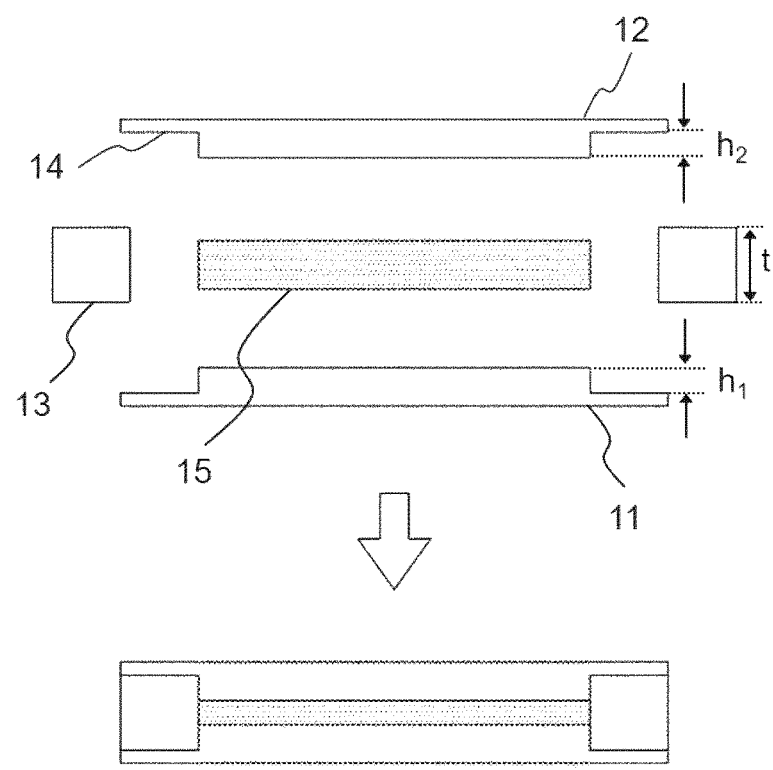

[FIG. 5]
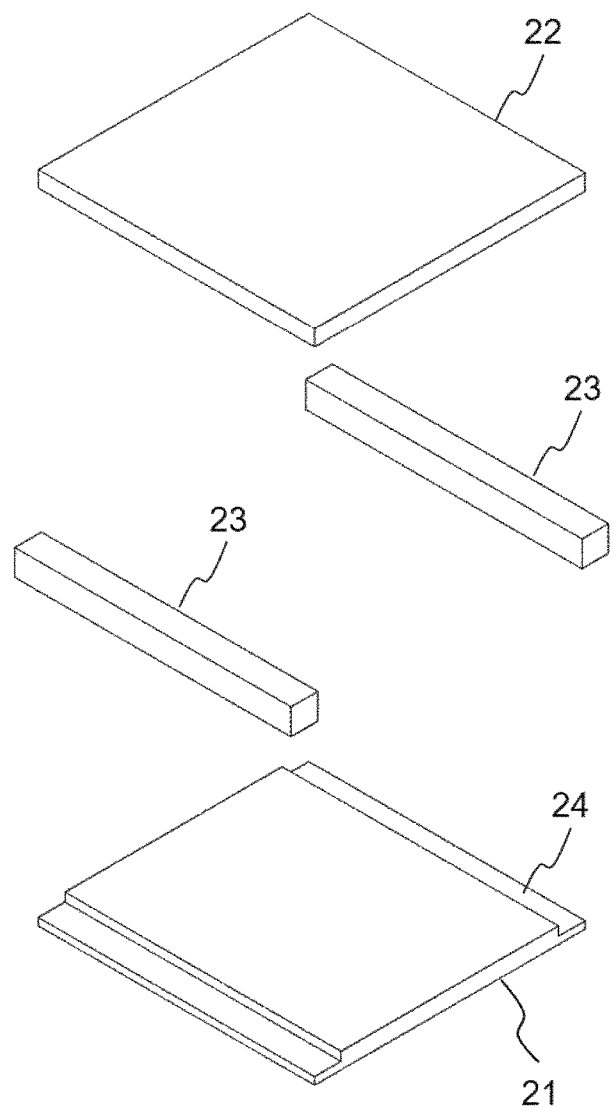

[FIG. 6]
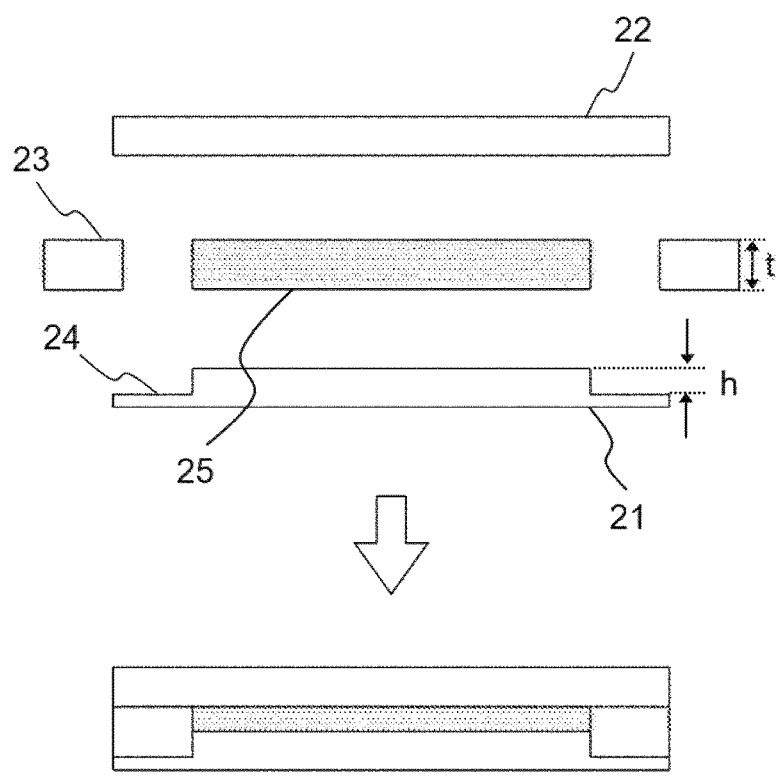

[FIG. 7]
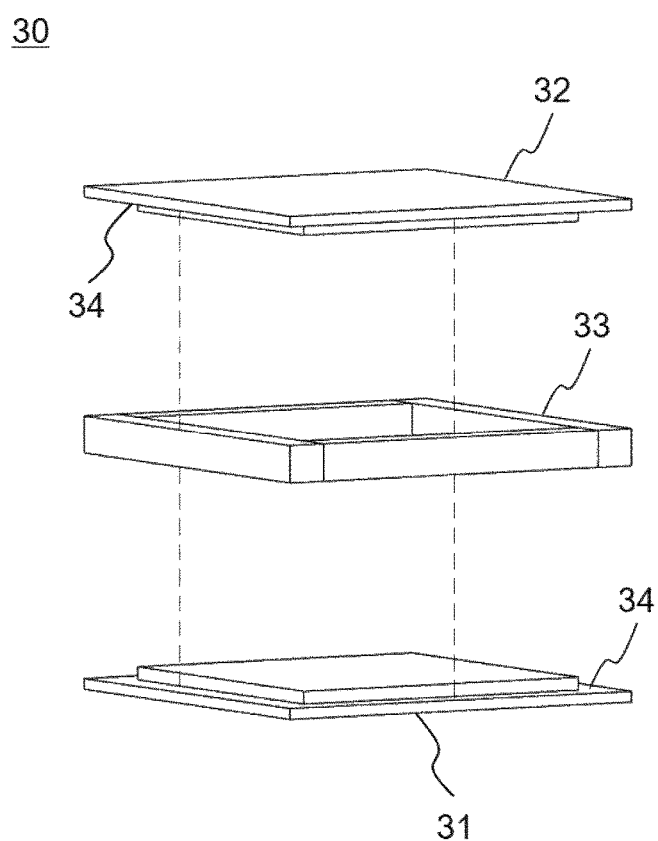

[FIG. 8]
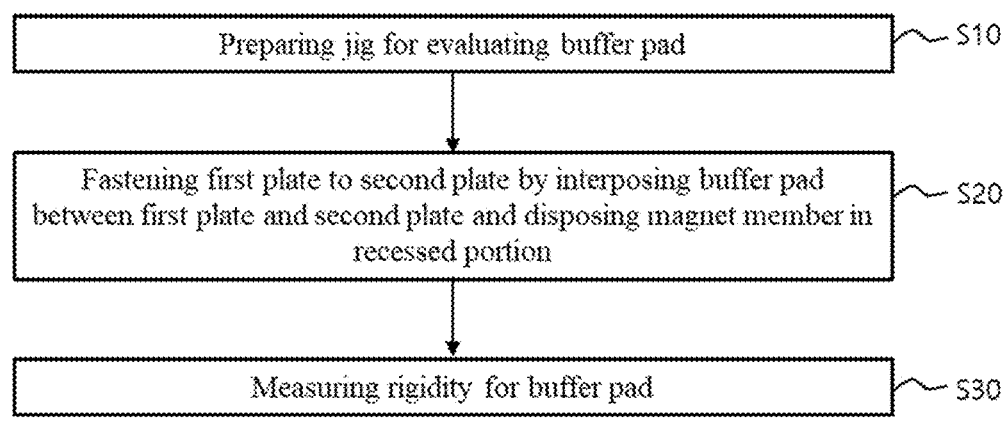

[FIG. 9]
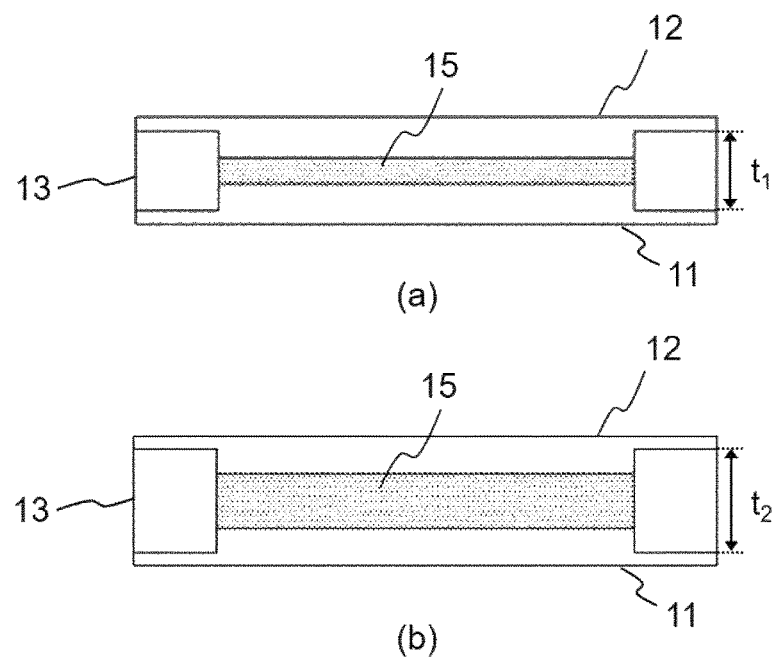

JIG FOR EVALUATING BUFFER PAD, AND METHOD OF EVALUATING BUFFER PAD USING THE SAME

TECHNICAL FIELD

This application claims the benefit of priority based on Korean Patent Application No. 10-2020-0119694, filed on Sep. 17, 2020, and the entire contents of the Korean patent application are incorporated herein by reference.

The present invention relates to a jig for evaluating a buffer pad, and a method of evaluating a buffer pad using the same, and more specifically to a jig for evaluating a buffer pad to be used for a battery module, and a method of evaluating a buffer pad to be used for a battery module.

BACKGROUND ART

Recently, secondary batteries capable of charging and discharging have been widely used as energy sources of wireless mobile devices. In addition, the secondary battery has attracted attention as an energy source of an electric vehicle, a hybrid electric vehicle, etc., which are proposed as a solution for air pollution of existing gasoline vehicles and diesel vehicles using fossil fuel. Therefore, the types of applications using the secondary battery are currently much diversified due to the advantages of the secondary battery, and it is expected that the secondary battery will be applied to many fields and products in the future.

Such a secondary battery may be classified into a lithium ion battery, a lithium ion polymer battery, a lithium polymer battery, etc., and may also be classified into a cylindrical battery or a prismatic battery where an electrode assembly is embedded in a cylindrical or prismatic metal can, and a pouch-type battery where an electrode assembly is embedded in a pouch-type case of an aluminum laminate sheet, according to the shape of the battery case. An electrode assembly embedded in a battery case is a rechargeable power generating element by including a positive electrode, a negative electrode, and a separator interposed between the positive electrode and the negative electrode, and may be classified into a jelly-roll type electrode assembly which is wound by interposing a separator between a long sheet-type positive electrode and negative electrode on which an active material has been applied, and a stack type electrode assembly which is obtained by sequentially laminating a plurality of positive electrodes and negative electrodes having a predetermined size in a state that a separator has been interposed therebetween.

Further, in order to increase the output and capacity of the battery cell, a plurality of battery cells are electrically connected to each other to form a packaged battery module. In particular, pouch-type secondary batteries are widely used in medium- to large-sized devices due to the advantage of easy stacking.

Such a battery module has a structure where a plurality of battery modules are accommodated in a module case, and in order to protect battery cells in the battery module from an impact or vibrations outside the module case, a buffer pad is interposed between the module case and the battery cells or between battery cells accommodated in the module case.

Further, information on the dynamic rigidity of a such a buffer pad is necessary for the dynamic structure analysis such as vibration analysis and impact analysis for the battery module. Particularly, since the rigidity of the buffer pad is different according to the compression rate, there is a need for a technology for measuring the dynamic rigidity while changing the compression rate.

Therefore, there is a need for a jig for charging and discharging a battery cell for solve the above problems.

DISCLOSURE

Technical Problem

The present invention is believed to solve at least some of the above problems. For example, an aspect of the present invention provides a jig for evaluating a buffer pad capable of evaluating the performance according to the compression rate of a buffer pad which is inserted into a battery module, and a method of evaluating a buffer pad using the jig.

Technical Solution

The present invention relates to a jig for evaluating a buffer pad, and the jig includes: a first plate which is positioned on one surface of the buffer pad and presses the buffer pad; a second plate which is positioned on an other surface of the buffer pad and presses the buffer pad from the other surface; and a magnet member which is positioned between the first plate and the second plate, in which a recessed portion, which is recessed to allow the magnet member to be disposed, is formed at an edge of at least one of the first plate and the second plate.

In a specific example, the first plate and the second plate are made of a metal material which responds to a magnet, and areas and sizes of the first plate and the second plate are same.

In a specific example, a shape of a portion contacting the recessed portion in the magnet member corresponds to a shape of the recessed portion to allow the magnet member to be closely attached to the recessed portion.

In one example, the recessed portion is formed at a partial region of an edge of the first plate or the second plate and is symmetrically formed based on a central portion of the plate.

At this time, a length and a width of a portion, where the recessed portion has been formed in the first plate or the second plate, corresponds to a length and a width of the magnet member.

In one example, a recessed portion may be formed at the first plate and the second plate, respectively.

At this time, a thickness of the magnet member is greater than a sum of a depth of the recessed portion formed in the first plate and a depth of the recessed portion formed in the second plate.

In another example, the recessed portion may be formed at one of the first plate and the second plate.

At this time, a thickness of the magnet member is greater than a depth of the recessed portion.

In another example, the recessed portion may be formed in an entire region of an edge of the first plate or the second plate.

At this time, a width of a portion, where the recessed portion has been formed in the first plate or the second plate, corresponds to a width of the magnet member.

Further, a thickness of an inner space surrounded by the first plate, the second plate and the magnet member may be equal to or less than a thickness of a target buffer pad.

Herein, an area of a horizontal section of an inner space surrounded by the first plate, the second plate and the magnet member may be equal to or greater than an area of a target buffer pad.

Further, the present invention provides a method of evaluating a buffer pad, and the method includes: preparing the above-described jig for evaluating a buffer pad; fastening a first plate to a second plate by interposing a buffer pad between the first plate and the second plate and disposing a magnet member in a recessed portion; and measuring a dynamic rigidity for the buffer pad.

In a specific example, the measuring of the dynamic rigidity includes measuring the dynamic rigidity according to a compression rate of the buffer pad by changing the compression rate of the buffer pad.

At this time, the compression rate of the buffer pad may be adjusted by a thickness of the magnet member.

Advantageous Effects

In the present invention, it is possible to easily adjust the compression rate of a buffer pad, which is inserted into a battery module, by using the magnet member, through which the dynamic rigidity according to the compression rate can be evaluated. Further, since the jig for evaluating a buffer pad according to the present invention has a simple structure, it is possible to minimize the influence by the jig at the time of evaluating a buffer pad.

BRIEF DESCRIPTION OF THE DRAWINGS

FIG. 1 is a photograph showing the shape of a buffer pad.

FIG. 2 is an exploded perspective view showing a structure of a jig for evaluating a buffer pad according to an embodiment of the present invention.

FIG. 3 is a perspective view showing a jig for evaluating a buffer pad in an assembled state according to one embodiment of the present invention.

FIG. 4 is a schematic diagram showing a shape in which a buffer pad has been fastened to a jig for evaluating a buffer pad according to an embodiment of the present invention.

FIG. 5 is an exploded perspective view showing a structure of a jig for evaluating a buffer pad according to another embodiment of the present invention.

FIG. 6 is a schematic diagram showing a shape in which a buffer pad has been fastened to a jig for evaluating a buffer pad according to another embodiment of the present invention.

FIG. 7 is an exploded perspective view showing a structure of a jig for evaluating a buffer pad according to another embodiment of the present invention.

FIG. 8 is a flowchart showing the procedure of a method for evaluating a buffer pad according to the present invention.

FIG. 9 is a schematic diagram illustrating a process of adjusting the compression rate of a pad in a method of evaluating a buffer pad according to the present invention.

DETAILED DESCRIPTION OF THE PREFERRED EMBODIMENTS

Hereinafter, the present invention will be described in detail with reference to the drawings. The terms and words used in the present specification and claims should not be construed as limited to ordinary or dictionary terms and the inventor may properly define the concept of the terms in order to best describe its invention. The terms and words should be construed as meaning and concept consistent with the technical idea of the present invention.

In this application, it should be understood that terms such as "include" or "have" are intended to indicate that there is a feature, number, step, operation, component, part, or a combination thereof described on the specification, and they do not exclude in advance the possibility of the presence or addition of one or more other features or numbers, steps, operations, components, parts or combinations thereof. Also, when a portion such as a layer, a film, an area, a plate, etc. is referred to as being "on" another portion, this includes not only the case where the portion is "directly on" the another portion but also the case where further another portion is interposed therebetween. On the other hand, when a portion such as a layer, a film, an area, a plate, etc. is referred to as being "under" another portion, this includes not only the case where the portion is "directly under" the another portion but also the case where further another portion is interposed therebetween. In addition, to be disposed "on" in the present application may include the case disposed at the bottom as well as the top.

Hereinafter, the present invention will be described in detail with reference to the drawings.

The present invention relates to a jig for evaluating a buffer pad, and the jig includes: a first plate which is positioned on one surface of the buffer pad and presses the buffer pad; a second plate which is positioned on an other surface of the buffer pad and presses the buffer pad from the other surface; and a magnet member which is positioned between the first plate and the second plate, in which a recessed portion, which is recessed to allow the magnet member to be disposed, is formed at an edge of at least one of the first plate and the second plate.

As described above, a buffer pad is interposed between a module case and a battery cell or between battery cells accommodated in the module case in order to protect battery cells in the module case from an impact or vibration outside the module case in a battery module. At this time, information on the dynamic rigidity of a such a buffer pad is necessary for the dynamic structure analysis such as vibration analysis and impact analysis for the battery module.

In the present invention, it is possible to easily adjust the compression rate of a buffer pad, which is inserted into a battery module, by using the magnet member, through which the dynamic rigidity according to the compression rate can be evaluated. Further, since the jig for evaluating a buffer pad according to the present invention has a simple structure, it is possible to minimize the influence by the jig at the time of evaluating a buffer pad.

Hereinafter, a jig for evaluating a buffer pad according to the present invention will be described in detail.

FIG. 1 is a photograph showing the shape of a buffer pad.

In the present invention, a buffer pad, which becomes a subject of evaluation, may be inserted into a battery module. Specifically, a plurality of battery cells are accommodated in the battery module. In particular, the battery cell may be a pouch-type battery cell, and the pouch-type battery cell may include an electrode assembly, an electrolyte solution, and a pouch case. Here, the electrode assembly is an assembly of an electrode and a separator, and may be configured in a form in which one or more positive electrode plates and one or more negative electrode plates are disposed with the separator interposed therebetween. In addition, each electrode plate of the electrode assembly is provided with an electrode tab, and one or more electrode tabs may be connected to the electrode lead. In addition, the electrode lead is interposed between the pouch case and one end is exposed to the outside, and the exposed portion may function as an electrode terminal of the secondary battery. The pouch case may contain an electrolyte solution together with the electrode assembly in the inner space. In addition, the pouch case may be configured in a form in which the edge portion is sealed by a method such as heat fusion. The pouch case may be composed of an upper pouch and a lower pouch, and each pouch includes an outer insulating layer, a metal layer, and an inner adhesive layer, so that the inner adhesive layers may be fused to each other.

The configuration of such a battery cell is obvious to a person skilled in the art to which the present invention pertains, and thus a more detailed description thereof will be omitted. In addition, various battery cells known at the time of filing the present invention may be employed in the battery pack according to the present invention.

A plurality of battery cells are mounted in a module case. The module case may be formed of a metal material having a high mechanical strength and excellent thermal conductivity.

Further, the battery module may be influenced by various kinds of vibrations and impacts from an outside while used. In order to prevent the battery cells accommodated in the module case from being damaged by such vibrations and impacts, a buffer pad is interposed between the battery cell and the module case or between battery cells.

Referring to FIG. 1, such a buffer pad may contain a material including a soft elastic material such as silicon, polyurethane, or Ethylene Propylene Diene Monomer (EPDM). In particular, a foam pad such as a polyurethane foam may be used as the buffer pad. Since such a material has excellent absorptiveness to vibration and repulsive power to compression, it is possible to effectively protect battery cells from external impacts and vibrations. In addition, such a buffer pad can act as a heat dissipation member when heat is generated from the battery cell.

Meanwhile, the jig for evaluating a buffer pad according to the present invention includes a pair of pressing plates where a buffer pad can be interposed.

Specifically, a jig for evaluating a buffer pad according to the present invention includes a first plate, which is positioned on one surface of a buffer pad and presses the buffer pad, and a second plate, which is positioned on the other surface of the buffer pad and presses the buffer pad from the other surface.

The first plate and the second plate may be made of a metal material responding to a magnet. Specifically, the first plate and the second plate may be made of one selected from the group consisting of iron, nickel, and cobalt, and more specifically be made of iron.

Further, the area and the thickness of the first and second plates may be appropriately designed according to the area and the thickness of the target buffer pad. However, the area of a portion, where the first and second plates contact the buffer pad, is preferably greater than the area of the buffer pad in consideration of the compression of the buffer pad. Further, the areas and sizes of the first and second plates may be the same to simplify the structure of the jig and minimize the influence of the jig on the evaluation. Herein, the area and size of the plate means the area and size of the outer periphery of the plate. For example, when the plate has a rectangular shape, the width of the plate may be the same as the length of the plate.

Further, the first plate and the second plate are fastened by a magnet member. Namely, since plates are fastened using magnets without fastening members such as brackets or bolts in the jig for evaluating a buffer pad according to the present invention, the structure is simple, and the influence of the jig may be minimized at the time of evaluating characteristics of the buffer pad. Further, as will be described later, since a separation distance between plates may be adjusted by adjusting the thickness of a magnet member, it is possible to easily adjust the compression rate of the buffer pad.

In the present invention, magnet member is positioned between the first plate and the second plate, a recessed portion, which is recessed to allow the magnet member to be disposed, is formed at the edge of the first plate and the second plate. More specifically, the recessed portion is formed at the edge of a surface where the first plate and the second plate contacts the buffer pad. Namely, the recessed portion has a shape recessed to have a predetermined width toward a central portion from the end of the first plate and the second plate. Likewise, the magnet can easily disposed at an appropriate position by forming a recessed portion at a portion where the magnet member is positioned.

A shape of a portion contacting the recessed portion in the magnet member corresponds to a shape of the recessed portion to allow the magnet member to be closely attached to the recessed portion. Herein, the fact that the shape of a portion contacting the recessed portion corresponds to the shape of the recessed portion means that the cross-sectional shape of the recessed portion is the same as the cross-sectional shape of the magnet member. For example, when the magnet member has a cuboid shape, the cross-sectional shape of the recessed portion also has a cuboid shape, and if the magnet member has a cylindrical shape, the recessed portion may also be recessed in a curved surface shape to have the same radius of curvature as that of the cylinder.

In one example, the recessed portion is formed at a partial region of the edge of the first plate or the second plate. Herein, the partial region of the edge means a part of the edge region formed along the circumference of the first plate or the second plate. At this time, the recessed portion may be symmetrically formed based on the central portion of the plate for stable fastening. For example, when the the first plate or the second plate have a quadrangle shape, the recessed portions may be formed on two sides facing each other.

At this time, a length and a width of a portion, where the recessed portion has been formed in the first plate or the second plate, corresponds to a length and a width of the magnet member. Namely, the recessed portion may be formed only on a portion of the plate contacting the magnet member, and the magnet member may be set to be closely attached to the inner wall of the recessed portion. However, the present invention is not limited to this example, and the area of the magnet member may be smaller than the area of the recessed portion.

In one example, a recessed portion may be formed at the first plate and the second plate, respectively. Namely, the first plate and the second plate may have the same shape, and the fixing jig has a vertically symmetrical structure. The magnet member is interposed between the recessed portion formed at the first plate and the recessed portion formed at the second plate. Likewise, since it is possible to manufacture only one type of plate by using the same shape for the first plate and the second plate, the manufacturing process of the plate and the fastening structure of the plate may become simple.

Likewise, when a recessed portion is formed at the first plate and the second plate, respectively, the thickness of the magnet member is preferably greater than the sum of the depth of the recessed portion formed at the first plate and the depth of the recessed portion formed at the second plate. This is to prepare a space where a buffer pad can be interposed between the first plate and the second plate. As will be described later, the compression rate of the buffer pad can be adjusted by adjusting the thickness of the space which is formed between the first and second plates by adjusting the thickness of the magnet member.

Further, the present invention is not limited thereto, and in another example, the recessed portion may be formed at any one of the first and second plates. In this case, the plate, where the recessed portion is not formed, may have a flat shape where irregularities are not formed on the surface.

Likewise, when the recessed portion is formed on any one of the first and second plates, the thickness of the magnet member is preferably greater than the depth of the recessed portion formed on any one of the first and second plates. This is to prepare a space where a buffer pad can be interposed between the first plate and the second plate. As will be described later, the compression rate of the buffer pad can be adjusted by adjusting the thickness of the space which is formed between the first and second plates by adjusting the thickness of the magnet member.

In another example, the recessed portion is formed in an entire region of an edge of the first plate or the second plate. Namely, the recessed portion may be formed on the entire edge region formed along the circumference of the first plate or the second plate. Likewise, by forming a recessed portion at the entire region of the edge of the plate and disposing the magnet member, it is possible to improve the fastening force between the first plate and the second plate and prevent the plate from being separated from the magnet member during the evaluation process. For example, when the first plate and the second plate have a quadrangle shape, the recessed portion may be formed on all four sides of the first plate or the second plate.

At this time, a width of a portion, where the recessed portion has been formed in the first plate or the second plate, may correspond to a width of the magnet member. The recessed portion may be formed only on a portion of the plate contacting the magnet member, and the magnet member may be set to be closely attached to the inner wall of the recessed portion. However, the present invention is not limited to this example, and the area of the magnet member may be smaller than the area of the recessed portion.

Further, as described above, a space, where a buffer pad may be interposed, is formed between the first plate, the second plate and the magnet member. At this time, a thickness of an inner space surrounded by the first plate, the second plate and the magnet member may be equal to or less than a thickness of a target buffer pad. This is to allow the buffer pad to be compressed in the space. When the thickness of the inner space is the same as the thickness of the buffer pad, it is possible to evaluate the buffer pad in a state that the buffer pad has not been compressed, and when the thickness of the inner space is smaller than the thickness of the buffer pad, it is possible to evaluate the buffer pad in a state that the buffer pad has been compressed.

Further, an area of a horizontal section of an inner space surrounded by the first plate, the second plate and the magnet member may be equal to or greater than an area of a target buffer pad. Herein, the area of the horizontal section means the cross-sectional area in a direction perpendicular to the lamination direction of the first plate and the second plate. Likewise, by setting the area of the horizontal section of the inner space surrounded by the first plate, the second plate and the magnet member to correspond to or be greater than the area of the buffer pad, it is possible to accommodate a portion where the area has increased when the area increases. For example, when the buffer pad, the first plate and the second plate have a quadrangle shape, the length of the width and the length of a space formed by the first plate, the second plate and the magnet member may be the same or greater than the length of the width and the length of the buffer pad.

Further, the present invention provides a method of evaluating a buffer pad, and the method includes: preparing the above-described jig for evaluating a buffer pad; interposing a buffer pad between a first plate and a second plate and disposing a magnet member in a recessed portion, so as to fasten the first plate to the second plate; and measuring a dynamic rigidity for the buffer pad.

First, a jig for evaluating a buffer pad as described above is prepared. The jig includes: a first plate which is positioned on one surface of the buffer pad and presses the buffer pad; a second plate which is positioned on an other surface of the buffer pad and presses the buffer pad from the other surface; and a magnet member which is positioned between the first plate and the second plate, in which a recessed portion, which is recessed to allow the magnet member to be disposed, is formed at an edge of at least one of the first plate and the second plate.

When the jig for evaluating a buffer pad is prepared, a buffer pad is interposed between the first plate and the second plate, and a magnet member is disposed in the recessed portion, to thereby fasten the first plate to the second plate.

Thereafter, dynamic rigidity of the buffer pad is measured. The dynamic rigidity means the degree of resistance to the displacement by a simple harmonic motion at an arbitrary point of a dynamical system. Herein, the simple harmonic motion includes a general vibration movement, etc.

In order to measure the dynamic rigidity of the buffer pad, a predetermined impact or vibration is applied to the buffer pad, and the degree of displacement at each point of the buffer pad and the degree of resistance to the displacement are measured. At this time, in order to prevent the interference from the ground on the buffer pad, it is preferred that the experiment is performed in a state that the buffer pad is suspended in midair.

Further, the dynamic rigidity of the buffer pad is changed according to the compression rate of the buffer pad. Hence, in the present invention, the step of measuring the dynamic rigidity includes a process of measuring the dynamic rigidity according to the compression rate of the buffer pad by changing the compression rate of the buffer pad.

Specifically, the compression rate of the buffer pad is adjusted by a thickness of the magnet member. For example, the compression rate of the compression rate can be increased by reducing the thickness of the inner space formed between the first plate, the second plate and the magnet member by reducing the thickness of the magnet. Further, the compression rate of the compression rate can be decreased by increasing the thickness of the inner space formed between the first plate, the second plate and the magnet member by increasing the thickness of the magnet. Namely, it is possible to measure the dynamic rigidity in a state that the buffer pad has been compressed.

Likewise, in the present invention, it is possible to easily adjust the compression rate of a buffer pad, which is inserted into a battery module, by using the magnet member, through which the dynamic rigidity according to the compression rate can be evaluated. Further, since the jig for evaluating a buffer pad according to the present invention has a simple structure, it is possible to minimize the influence by the jig at the time of evaluating a buffer pad.

As the inventive concept allows for various changes and numerous embodiments, particular embodiments will be illustrated in the drawings and described in detail in the text. However, this is not intended to limit the present invention to the specific form disclosed, and it should be understood to include all changes, equivalents, and substitutes included in the spirit and scope of the present invention.

First Embodiment

FIG. 2 is an exploded perspective view showing a structure of a jig for evaluating a buffer pad according to an embodiment of the present invention, and FIG. 3 is a perspective view showing a jig for evaluating a buffer pad in an assembled state according to one embodiment of the present invention. FIG. 4 is a schematic diagram showing a shape in which a buffer pad has been fastened to a jig for evaluating a buffer pad according to an embodiment of the present invention.

Referring to FIGS. 2 to 4, a jig 10 for evaluating a buffer pad according to the present invention includes: a first plate 11 which is positioned on one surface of the buffer pad 15 and presses the buffer pad 15; a second plate 12 which is positioned on an other surface of the buffer pad 15 and presses the buffer pad 15 from the other surface; and a magnet member 13 which is positioned between the first plate 11 and the second plate 12. The first plate 11 and the second plate 12 may be made of a metal material responding to a magnet.

A magnet member 13 for fastening the first plate 11 to the second plate 12 is positioned between the first plate 11 and the second plate 12. Further, a recessed portion 14, which is recessed to allow the magnet member to be disposed, is formed at the edge of at least one of the first plate 11 and the second plate 12.

The shape of a portion contacting the recessed portion 14 in the magnet member 13 corresponds to the shape of the recessed portion 14 to be completely attached to the recessed portion 14. Referring to FIGS. 2 to 4, the cross-section of the magnet member 13 has a quadrangle shape, and accordingly it is illustrated that the cross-section of the recessed portion 14 also has a quadrangle shape.

The recessed portion 14 is formed at a partial region at the edge of the first plate 11 or the second plate 12. Further, the recessed portion 14 is formed at the first plate 11 and the second plate 12, respectively. In FIGS. 2 and 3, the recessed portion 14 is formed on two sides facing each other among 4 sides of the first plate 11 and the second plate 12 having a quadrangle shape. At this time, the length ($l_1$) and the width ($w_1$) of a portion, where the recessed portion 14 has been formed in the first plate 12 and the second plate 12, correspond to the length ($l_2$) and the width ($w_2$) of the magnet member 13. Further, in order to prepare a space where the buffer pad 15 can be interposed between the first plate 11 and the second plate 12, the thickness (t) of the magnet member 13 is greater than the sum of the depth ($h_1$) of the recessed portion formed on the first plate 11 and the depth ($h_2$) of the recessed portion 14 formed on the second plate 12.

Further, referring to FIG. 4, the buffer pad 15 is interposed in the inner space between the first plate 11, the second plate 12 and the magnet member 13. At this time, the thickness of the inner space may be equal to or smaller than the thickness of the target buffer pad 15, and the area of the horizontal section of the inner space may correspond to or be greater than the area of the buffer pad 15.

Second Embodiment

FIG. 5 is an exploded perspective view showing a structure of a jig for evaluating a buffer pad according to another embodiment of the present invention, and FIG. 6 is a schematic diagram showing a shape in which a buffer pad has been fastened to a jig for evaluating a buffer pad according to another embodiment of the present invention.

Referring to FIGS. 5 and 6, a jig 20 for evaluating a buffer pad according to the present invention includes: a first plate 21 which is positioned on one surface of the buffer pad 25 and presses the buffer pad 25; a second plate 22 which is positioned on an other surface of the buffer pad 25 and presses the buffer pad 25 from the other surface; and a magnet member 23 which is positioned between the first plate 21 and the second plate 22. Further, a recessed portion 24, which is recessed to allow the magnet member 23 to be disposed, is formed at the edge of at least one of the first plate 21 and the second plate 22.

Referring to FIGS. 5 and 6, the recessed portion 24 is formed at a partial region of the first plate 21 or the second plate 22. For example, the recessed portion 24 is formed on two sides facing each other among sides of the first plate 21 and the second plate 22. Further, the recessed portion 24 is formed at one of the first plate 21 and the second plate 22. Referring to FIGS. 5 and 6, the recessed portion 24 is formed on only the first plate 21. In order to prepare a space where a buffer pad 25 can be interposed between the first plate 21 and the second plate 22, the thickness (t) of the magnet member 23 may be greater than the depth (h) of the recessed portion 24 formed on the first plate 21.

Further, referring to FIG. 6, the buffer pad is interposed in the inner space between the first plate 21, the second plate 22 and the magnet member 23. At this time, the thickness of the inner space may be equal to or smaller than the thickness of the target buffer pad 25, and the area of the horizontal section of the inner space may correspond to or be greater than the area of the buffer pad 25.

Third Embodiment

FIG. 7 is an exploded perspective view showing a structure of a jig for evaluating a buffer pad according to another embodiment of the present invention.

Referring to FIG. 7, a jig 30 for evaluating a buffer pad according to the present invention includes: a first plate 31 which is positioned on one surface of the buffer pad (not shown) and presses the buffer pad; a second plate 32 which is positioned on an other surface of the buffer pad and presses the buffer pad from the other surface; and a magnet member 33 which is positioned between the first plate 31 and the second plate 32. Further, a recessed portion 34, which is recessed to allow the magnet member 33 to be disposed, is formed at the edge of at least one of the first plate 31 and the second plate 32.

Referring to FIG. 7, the recessed portion 34 is formed at the entire region of the edges of the first plate 31 or the second plate 32. For example, the recessed portion 34 is formed on all four sides of the first plate 31 and the second plate 32. Further, FIG. 7 shows the recessed portion 34 which is respectively formed in the first plate 31 and the second plate 32.

Referring to FIG. 7, the magnet member 33 is configured to be disposed in the entire recessed region or may be integrally formed, and may also be disposed as a plurality of magnet members in the region as shown in FIG. 7. At this time, a width of a portion, where the recessed portion 34 has been formed in the first plate 31 and the second plate 32, corresponds to a width of the magnet member 33.

Fourth Embodiment

FIG. 8 is a flowchart showing the procedure of a method for evaluating a buffer pad according to the present invention.

Referring to FIG. 8, the method of evaluating a buffer pad includes: preparing the above-described jig for evaluating a buffer pad (S10); interposing a buffer pad between a first plate and a second plate and disposing a magnet member in a recessed portion, so as to fasten the first plate to the second plate (S20); and measuring a dynamic rigidity for the buffer pad (S30).

FIG. 9 is a schematic diagram illustrating a process of adjusting the compression rate of a buffer pad in a method of evaluating a buffer pad according to the present invention.

Referring to FIG. 9, the buffer pad 15 is interposed in the space between the first plate 11 and the second plate 12 constituting the jig 10 for evaluating a buffer pad. Thereafter, if the magnet member 13 is disposed on the recessed portion 14, the buffer pad 15 is compressed by applying force to the first plate 11 and the second plate 12. In this state, the jig 10 for evaluating a buffer pad is suspended in midair, and the dynamic rigidity of the buffer pad 15 is measured.

At this time, the measuring of the dynamic rigidity includes measuring the dynamic rigidity according to a compression rate of the buffer pad 15 by changing the compression rate of the buffer pad 15.

Specifically, referring to FIG. 9, the compression rate is adjusted by the thickness of the magnet member 13. FIG. 9(a) shows a case that the compression rate of the buffer pad 15 has been increased by reducing the thickness ($t_1$) of the magnet member 13, and FIG. 9(b) shows a case that the compression rate of the buffer pad 15 has been reduced by increasing the thickness ($t_2$) of the magnet member 13.

The above description is merely illustrative of the technical idea of the present invention, and those skilled in the art to which the present invention pertains may make various modifications and variations without departing from the essential characteristics of the present invention. Therefore, the drawings disclosed in the present invention are not intended to limit the technical idea of the present invention but to describe the present invention, and the scope of the technical idea of the present invention is not limited by these drawings. The scope of protection of the present invention should be interpreted by the following claims, and all technical ideas within the scope equivalent thereto should be construed as being included in the scope of the present invention.

On the other hand, in this specification, terms indicating directions such as up, down, left, right, before, and after are used, but it is obvious that these terms are for convenience of description only and may change depending on the location of the object or the location of the observer.

The invention claimed is:

1. A jig for evaluating a buffer pad, the jig comprising:
    a first plate configured to be positioned on one surface of the buffer pad and configured to press the buffer pad;
    a second plate configured to be positioned on another surface of the buffer pad and configured to press the buffer pad from the other surface; and
    a magnet member configured to be positioned between the first plate and the second plate,
    wherein a recessed portion, which is recessed to allow the magnet member to be disposed, is defined at an edge of at least one of the first plate and the second plate,
    wherein a recessed portion is defined at the first plate and the second plate, respectively, and
    wherein a thickness of the magnet member is greater than a sum of a depth of the recessed portion defined in the first plate and a depth of the recessed portion defined in the second plate.

2. The jig of claim 1, wherein the first plate and the second plate include a metal material which responds to a magnet, and wherein areas and sizes of the first plate and the second plate are same.

3. The jig of claim 1, wherein a shape of a portion contacting the recessed portion in the magnet member corresponds to a shape of the recessed portion to allow the magnet member to be closely attached to the recessed portion.

4. The jig of claim 1, wherein the recessed portion is defined at a partial region of an edge of the first plate or the second plate and is symmetrical with respect to a central portion of the plate.

5. The jig of claim 4, wherein a length and a width of the recessed portion defined in the first plate or the second plate corresponds to a length and a width of the magnet member.

6. The jig of claim 1, wherein the recessed portion is defined in an entire region of an edge of the first plate or the second plate.

7. The jig of claim 6, wherein a width of the recessed portion of the first plate or the second plate corresponds to a width of the magnet member.

8. The jig of claim 1, wherein a thickness of an inner space surrounded by the first plate, the second plate, and the magnet member is equal to or less than a thickness of a target buffer pad.

9. The jig of claim 1, wherein an area of a horizontal section of an inner space surrounded by the first plate, the second plate and the magnet member is equal to or greater than an area of a target buffer pad.

10. The jig of claim 1, wherein the recessed portion is defined in an entire region of an edge of the first plate or the second plate.

11. The jig of claim 10, wherein a width of the recessed portion of the first plate or the second plate corresponds to a width of the magnet member.

12. A jig for evaluating a buffer pad, the jig comprising:
    a first plate configured to be positioned on one surface of the buffer pad and configured to press the buffer pad;
    a second plate configured to be positioned on another surface of the buffer pad and configured to press the buffer pad from the other surface; and
    a magnet member configured to be positioned between the first plate and the second plate,
    wherein a recessed portion, which is recessed to allow the magnet member to be disposed, is defined at an edge of at least one of the first plate and the second plate, and
    wherein the recessed portion is defined at only one of the first plate and the second plate.

13. The jig of claim 12, wherein a thickness of the magnet member is greater than a depth of the recessed portion.

14. The jig of claim 12, wherein the first plate and the second plate include a metal material which responds to a magnet, and wherein areas and sizes of the first plate and the second plate are same.

15. The jig of claim 12, wherein a shape of a portion contacting the recessed portion in the magnet member corresponds to a shape of the recessed portion to allow the magnet member to be closely attached to the recessed portion.

16. The jig of claim 12, wherein the recessed portion is defined at a partial region of an edge of the first plate or the second plate and is symmetrical with respect to a central portion of the plate.

17. The jig of claim 16, wherein a length and a width of the recessed portion defined in the first plate or the second plate corresponds to a length and a width of the magnet member.

18. The jig of claim 12, wherein a thickness of an inner space surrounded by the first plate, the second plate, and the magnet member is equal to or less than a thickness of a target buffer pad.

19. The jig of claim 12, wherein an area of a horizontal section of an inner space surrounded by the first plate, the second plate, and the magnet member is equal to or greater than an area of a target buffer pad.

* * * * *